United States Patent [19]
Barbour et al.

[11] Patent Number: 5,890,095
[45] Date of Patent: Mar. 30, 1999

[54] SYSTEM FOR RECEIVING AND ENHANCING ELECTROMAGNETIC RADIATION INPUT SIGNALS

[75] Inventors: Blair A. Barbour, Madison, Ala.; David B. Chenault, Mary Ester, Fla.

[73] Assignee: Nichols Research Corporation, Huntsville, Ala.

[21] Appl. No.: 785,090

[22] Filed: Jan. 21, 1997

[51] Int. Cl.$^6$ ..................................................... G01N 21/21
[52] U.S. Cl. ............................ 702/40; 702/106; 702/134; 356/351; 356/364; 250/559.09; 250/341.3
[58] Field of Search .................................... 364/525, 526, 364/550, 551.01, 571.01, 559; 340/580, 583; 348/61, 143; 356/50, 51, 351, 352, 364–368, 350, 346; 250/341.8, 341.3, 341.5, 342, 255, 559.09, 559.1, 225; 244/134 R, 134 F; 372/22; 359/494, 500, 483, 485, 486; 702/28, 38, 40, 49, 104, 106, 107, 134, 135, 150, 159, 172, 189; 382/191, 286, 307

[56] References Cited

U.S. PATENT DOCUMENTS

| | | | |
|---|---|---|---|
| 4,698,816 | 10/1987 | Chun | 359/483 |
| 4,997,282 | 3/1991 | Pavlath | 356/350 |
| 5,117,433 | 5/1992 | Tatsuno et al. | 372/22 |
| 5,311,285 | 5/1994 | Oshige et al. | 356/367 |
| 5,337,146 | 8/1994 | Azzam | 250/225 |
| 5,345,308 | 9/1994 | Bushman | 250/342 |
| 5,367,403 | 11/1994 | Yamamoto et al. | 359/494 |
| 5,406,371 | 4/1995 | Sakai et al. | 356/364 |
| 5,521,705 | 5/1996 | Oldenbourg et al. | 356/368 |
| 5,557,261 | 9/1996 | Barbour | 340/580 |
| 5,638,200 | 6/1997 | Xu | 359/494 |

*Primary Examiner*—Hal Dodge Wachsman

[57] ABSTRACT

A spatial phase sensor having a lens or opening, or the like, through which electromagnetic radiation signals are directed. Mechanism is provided for receiving the electromagnetic radiation signals and for providing an enhanced electrical signal therefrom. The spatial phase of the electromagnetic radiation signals is first determined by analysis of the polarization vectors of the electromagnetic radiation signals and a sensor is provided for converting the electromagnetic radiation signals into electrical signals containing data corresponding to the determined spatial phase of the electromagnetic signals.

20 Claims, 5 Drawing Sheets

| 1 | 2 | 3 | 4 | 1 | 2 | 3 | 4 |
|---|---|---|---|---|---|---|---|
| 3 | 4 | 1 | 2 | 3 | 4 | 1 | 2 |
| 1 | 2 | 3 | 4 | 1 | 2 | 3 | 4 |
| 3 | 4 | 1 | 2 | 3 | 4 | 1 | 2 |

FIG. 6a

| 1 | 2 | 3 | 4 | 5 | 6 | 7 | 8 |
|---|---|---|---|---|---|---|---|
| 5 | 6 | 7 | 8 | 1 | 2 | 3 | 4 |
| 3 | 4 | 5 | 6 | 7 | 8 | 1 | 2 |
| 7 | 8 | 1 | 2 | 3 | 4 | 5 | 6 |

FIG. 6b

| 1 | 2 | 3 | 4 |
|---|---|---|---|
| 5 | 6 | 7 | 8 |

FIG. 6c

| 1 | 2 |
|---|---|
| 5 | 6 |
| 3 | 4 |
| 7 | 8 |

FIG. 6e

| 2 | 3 | 4 | 5 |
|---|---|---|---|
| 6 | 7 | 8 | 1 |

FIG. 6d

| 5 | 6 |
|---|---|
| 3 | 4 |
| 7 | 8 |
| 1 | 2 |

FIG. 6f

| | | | |
|---|---|---|---|
| | | | |
| | | | |
| | | | |

FIG. 6g

SYSTEM FOR RECEIVING AND ENHANCING ELECTROMAGNETIC RADIATION INPUT SIGNALS

FIELD OF THE INVENTION

This invention generally relates to data and/or images which are separated into multiple spatial phase components. The spatial phase components are developed from full polarized electromagnetic radiation including light to produce enhanced data sets of a scene or area of interest in the form of data and/or images.

BACKGROUND OF THE INVENTION

All electro-magnetic radiation has a polarization vector associated with it. This vector is a complex two-dimensional spatial vector. The vector is contained within a plane that is perpendicular to the direction of propagation of the electric field. Within this plane, however, the vector may have any orientation. The complex nature of the vector stems from the fact that the orientation and magnitude of the vector may change with time, sweeping out an ellipse. Spatial phase vectors are present across the entire EM spectrum as well as for emitted, reflected and transmitted radiation and the devices to be described herein need not be limited to a single region of the spectrum.

The spatial phase of EM radiation emanating from the surface of an object, whether it is emitted, transmitted, or reflected, has a measurable spatial phase. Thus the shape of the object, the type of material from which it is made, the orientation of the object relative to the observer, etc., all effect the spatial phase of EM radiation emanating from the object. As a result, the various objects within a scene will each have a distinct spatial phase signature.

Most detection systems, especially imaging systems, measure the amplitude of the emitted EM radiation while ignoring the spatial phase of this radiation. However, there is inherently more information contained within the spatial phase than in the amplitude alone and sensors which can measure the spatial phase vector will have greater detection and discrimination capability than those which simply measure the amplitude. Illustrating this point is the fact that the amplitude information can be derived from the spatial phase data. The converse is not true.

Measuring the spatial phase of a light beam requires several optical elements in addition to those required for amplitude detection. These additional elements include but are not limited to polarizers and retarder plates. These two elements are complimentary and when used together can accurately measure the spatial phase of light incident on them.

Polarizers transmit a fixed spatial phase state independent of the incident spatial phase, in effect, filtering the incident light. Although the spatial phase of the transmitted light is independent of the incident spatial phase, the intensity of the transmitted radiation does depend on the incident state. A retarder, on the other hand, modifies the spatial phase but does not perform any filtering functions. The spatial phase transmitted by a retarder is dependent on the spatial phase of the incident light while the transmitted intensity is independent of the spatial phase of the incident radiation.

Quantitative analysis of the spatial phase of a light beam requires a mathematical formalism for describing the polarization state of radiation and the polarization altering properties of polarization elements. The principal computational methods for treating polarization problems are the Stokes elements, Jones calculus and the Mueller calculus.

The polarization state of radiation is described by the Stokes vector, a four element real vector:

$$S = \begin{matrix} S_0 \\ S_1 \\ S_2 \\ S_3 \end{matrix} = S_0 \begin{matrix} 1 \\ s_1 \\ s_2 \\ s_3 \end{matrix} \tag{1}$$

where the lower case letters represent elements normalized by the first element of the vector $S_0$. The units of the Stokes vector are intensity. The first element of the Stokes vector $S_0$ gives the intensity of the radiation and is the only element that is directly measurable by experiment. The other three elements of the Stokes vector $S_1$, $S_2$ and $S_3$ describe the polarization state of the radiation and give the "preference" for horizontal, ±45°, and right/left circular polarized radiation.

Formally, the $S_1$ element represents the difference in intensities for horizontally and vertically polarized radiation, the $S_2$ element is the difference in intensities for radiation polarized along the ±45° axes, and $S_3$ is the difference of right/left circularly polarized radiation. For the normalized Stokes vector, the elements range from 1 to −1. The $S_1$ element takes on a value of 1 for completely horizontally polarized radiation and is −1 for completely vertically polarized radiation. Similarly, the $S_2$ element is 1 and −1 for ±45° and −45° polarized radiation, and $S_3=1$ represents right circular radiation and $S_3=-1$ is left circular. The degree of polarization is found from:

$$DOP = S_1 + S_2 + S_2/S_0$$
$$DOLP = S_1 + S_2/S_0 \tag{2}$$
$$DOCP = |S_3|/S_0$$

where DOP is the degree of polarization including linear and circular polarization, DOLP is the degree of linear polarization, and DOCP is the degree of circular polarization. DOP=1 represents totally polarized radiation, DOLP=1 represents totally linear polarized radiation, and DOCP=1 is totally circularly polarized radiation.

Additional polarization vector metrics that may be obtained from the Stokes vectors are $$DOUP = 1 - DOP \tag{3}$$
$$\Theta = 1/2 \tan^{-1}(S_2/S_1)$$
$$\text{ellipticity} = \frac{DOP - DOLP}{DOP + DOLP}$$

where DOUP is the degree to which the light is unpolarized, $\Theta$ is the orientation of the major axis of the polarization vector, and ellipticity is a measure of the relative magnitude of the major and minor axes. The spatial phase of radiation is defined by the complete set of polarization metrics.

Devices which measure the spatial phase of the EM radiation which is incident on them are referred to as polarimeters or polarization state analyzers. Conventional polarimeters measure the area average of the spatial phase for a beam of light. Variations of the spatial phase from point to point within the beam are averaged. An imaging polarimeter is a special class of devices in which the variations of the spatial phase from point to point within a beam of light (or equivalently from point to point within a scene or across an object) are measured. A two dimensional array of detectors is used for this device instead of a single detector as used in conventional polarimetry.

The spatial phase cannot be measured directly but may be calculated from a set of complimentary intensity measurements. There are numerous measurement sets from which the spatial phase may be calculated, each of which requiring a separate calculation method. For clarity, the methods described herein will first calculate the Stoke's vectors and then the polarization metrics. The Stoke's vectors are intermediary and need not necessarily be calculated.

Two approaches for obtaining the Stokes vector are described below. For consistency the approaches will be described for an imaging polarimetry system as disclosed herein.

The first approach for obtaining a set of complimentary intensity measurements includes the use of a sensor such as a focal plane array, an imaging lens, a ¼-waveplate, and a polarizer, as discussed in detail hereinbelow. The waveplate is placed in front of the polarizer. The waveplate/polarizer combination may be placed either in front of the lens or between the lens and the sensor. An image is acquired at a finite number of regularly spaced angular positions of the waveplate (for example 16). The 16 intensity measurements for a given pixel (corresponding to a single object point) will sweep out a curve as a function of the angular position of the waveplate.

This curve is characteristic of the spatial phase of the radiation for that object point and may be analyzed to determine the Stokes parameters as well as a number of other polarization metrics. This analysis may be performed in two ways (1) using a measurement matrix and (2) performing a Fast Fourier Transform (FFT) on the data and making a few calculations. The FFT method is outlined below.

Linear polarized light produces a signal that has four maxima and minima and will appear in the fourth harmonic component of the FFT data. The orientation of the linearly polarized signal determines the phase of the fourth harmonic component as well as contributes to the DC component. Circularly polarized produces two maxima and minima and will appear in the second harmonic component of the FFT data. The handedness (i.e. clockwise rotation or counter clockwise rotations) determines the phase of the second harmonic component. Unpolarized light produces a DC signal that appears in the DC component of the FFT data. The relative amplitudes of these components determine the degree to which the light is linear polarized circularly polarized, etc.

These effects can be quantitatively determined from the following equations. The parameters of the Stokes vector are obtained using $$S_0 = \frac{A_0}{2} - A_4 \quad (4)$$

$$S_1 = 2A_4$$

$$S_2 = 2B_4$$

$$S_3 = -B_2$$

where $A_0$ and $A_4$ are the real parts of the DC and fourth harmonic components respectively and $B_2$ and $B_4$ are the imaginary components of the second and fourth harmonic components. It should be noted that the polarization metrics can be calculated directly from the FFT data without calculating the intermediate Stokes vectors.

The second approach for obtaining a set of complimentary images is to measure the intensity emitted (or reflected) from an object through a series of four filters. The choice of the filters is not unique. One particularly intuitive and insightful set of filters is (1) a polarizer at 0°, (2) a polarizer at 45°, (3) a quarter wave retarder (or equivalently a ¼ λ wave-plate which converts circular polarized light into linear polarized light) and polarizer, and (4) a 50% transmitting neutral density filter.

The intensity detected through each filter is denoted by the vector I.

$$I = \begin{matrix} I_0 \\ I_1 \\ I_2 \\ I_3 \end{matrix} \quad (5)$$

where $I_0$ is the intensity passed by the neutral density filter, $I_1$ is the intensity passed by the 0° polarizer, $I_2$ is the intensity passed by the 45° polarizer, and $I_3$ is the intensity passed by the ¼ wave plate and polarizer. The Stokes' vectors are then defined as $$S_0 = 2I_0$$

$$S_1 = 2I_1 - 2I_0$$

$$S_2 = 2I_2 - 2I_0$$

$$S_3 = 2I_3 - 2I_0$$

As with the FFT method, all of the polarization vector metrics may be calculated directly from the intensity vector I without necessarily calculating the intermediate Stokes vectors.

A prior art patent, incorporated herein by reference, was issued to a co-inventor, Blair A. Barbour, on Sep. 17, 1996. This patent is U.S. Pat. No. 5,557,261 and is entitled "Ice Monitoring And Detection System" and discloses the use of polarized images to detect the presence and amount of ice on a surface. The system as disclosed in U.S. Pat. No. 5,557,261 uses a rotating polarizer in one embodiment and camera having two different lenses and focal plane arrays in a second embodiment. U.S. Pat. No. 5,557,261 is not concerned with enhancing signals which form the image.

SUMMARY OF THE INVENTION

The present invention utilizes the principles of polarized radiation to provide an image/data of an area of interest. The image is enhanced by the use of "super" pixels. Each "super" pixel is defined by an array of at least four adjoining pixels each of which is polarized in different states (For example, 0°, 90°, +45°, −45°). Such a pixel array collects all the intensity measurements required to calculate the spatial phase at the same time and provides a single "super" pixel output, at the point of adjoinment of the pixels, which is a resultant of the four adjoining pixels. As will appear hereinbelow many different patterns of the pixels may be utilized in producing pluralities of "super" pixels.

Electronic circuitry is provided for processing the output of the super pixel/pixels to produce a video image of the area of interest which has a greatly enhanced resolution.

It is, therefore, an object of the present invention to provide a video device for producing a spatial phase image having enhanced signal contrast, thereby providing an image of an area of interest with a higher degree of sharpness and clarity otherwise unobtainable.

It is also an object of the present invention to provide such enhanced signal strength by the use of super pixels.

BRIEF DESCRIPTION OF THE DRAWINGS

FIG. 2a illustrates an array of pixels and the grouping thereof to form "super" pixels. The heavy line outlines a group of pixels which form the "super" pixel.

FIG. 2b is an array of "super" pixels formed from the array of pixels illustrated in FIG. 2a.

FIGS. 6a–6g are diagrammatical views of different patterns of polarization grids mounted on the surface of the focal plane array of FIG. 1 to provide pluralities of "super" pixels.

DESCRIPTION OF THE PREFERRED EMBODIMENTS

Figure 1:
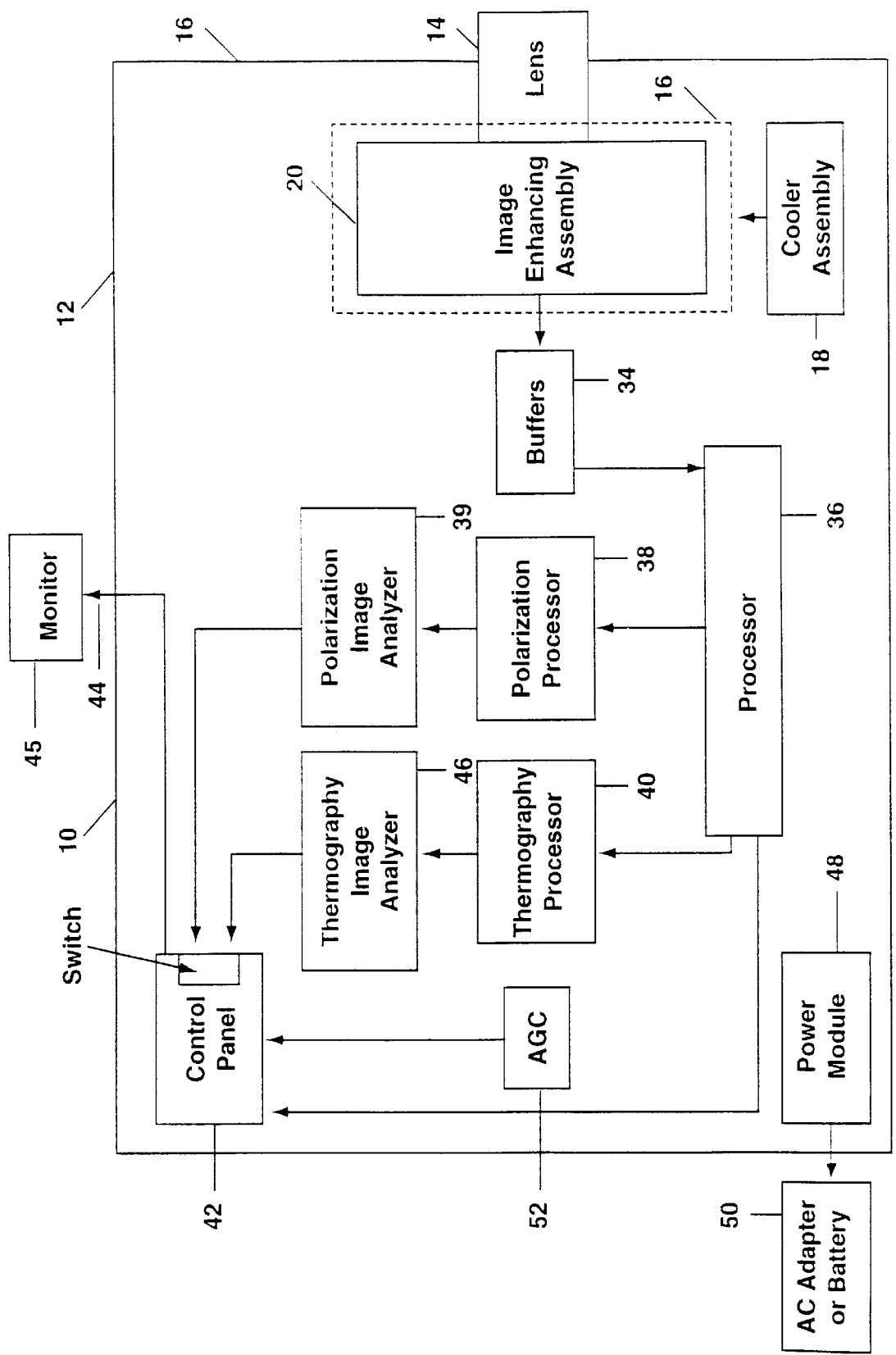
FIG. 1 is a block diagram of a camera utilizing the principles of the present invention.

A device 10 for providing an image of an object or area of interest is illustrated in FIG. 1. The device is diagrammatically shown to be a video camera which includes a housing 12 having a lens 14 at the front surface 15 thereof. Lens 14 communicates into a Dewar assembly 16 which communicates with a cooler assembly 18 to provide coolant to components therein. Such Dewar assemblies are well known in the art. Carried in Dewar assembly 16 is an image enhancing assembly 20 which receives the image refracted, through lens 14, from the object or area of interest and polarizes the image in a manner which will produce super pixels which greatly increases the signal strength of the image.

The specific function of the image enhancing means 20 is to form a plurality of pixels in predetermined patterns so that each pattern consists of at least four pixels formed in two rows and two columns with each pixel having different polarization vectors and the resultant output therefrom being taken from the point of adjoinment of the pixels in the form of a single output. A plurality of "super" pixels are formed in columns and rows by adjoining pluralities of the thus formed "super" pixels.

Figure 2A:
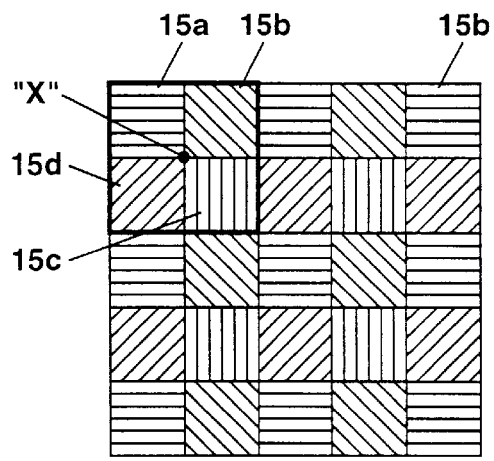
FIG. 2a is an illustration of the "super" pixel formation of the present invention.
Figure 2B:
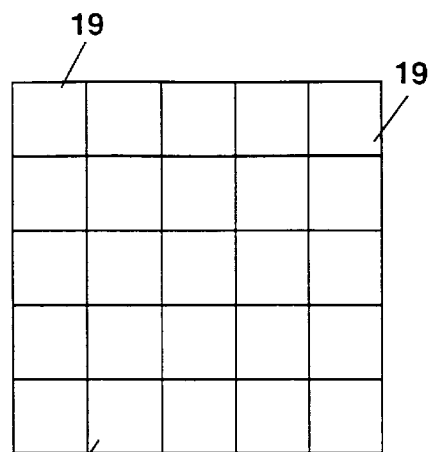

FIGS. 2a and 2b illustrate the formation of the "super" pixels. For illustrative purposes (FIG. 2a), a pattern 15 of pixels (each containing thermal and polarization data) are shown in a 5×5 pixel array. A "super" pixel (FIG. 2a) is shown to be formed by the adjoining pixels 15a, 15b, 15c and 15d. The point "X" at which the four pixels 15a, 15b, 15c and 15d join represents the single output of the four pixels. 2×2 sample patterns are repeated. The 2×2 pattern is digitized every center pixel thereby maintaining the resolution of the array. The pattern can be repeated to form an n×n array. The patterns may also have subset patterns. For example, a 4×4 pattern may also be sampled with a 2×2 subse.

FIG. 2b illustrates an array of resultant ("super") pixels collected at each point "X" as shown in FIG. 2a. The resultant array of "super" pixels is depicted in FIG. 2b and is illustrative of any n×n array. Each resultant pixel contains polarization and thermal data of the area of interest.

A lenslet 22 (FIG. 3) is shown to be mounted behind lens 14 and is a part of an image enhancing assembly 20 including a retarder plate 26, a polarization matrix (wire grid) 28 and a sensor such as a focal plane array 30. Polarization matrix 28 should be mounted close to the sensor 30. Sensor 30 receives the image data and converts this data into electrical signals. A calibration device 32 may, if desired, be mounted intermediate the assembly 24 and lens 14 to calibrate the device. Such calibration device is described hereinbelow.

Retarder plate 26 typically is made of a material which is naturally birefringent. However, it is to be understood that the present invention contemplates a retarder plate which is comprised of a non-naturally birefringent material having a predetermined pattern of subwavelength grooves therein. Such structure produces a formed birefringent and thereby provides an achromatic retardation plate analyzer.

Figure 3:
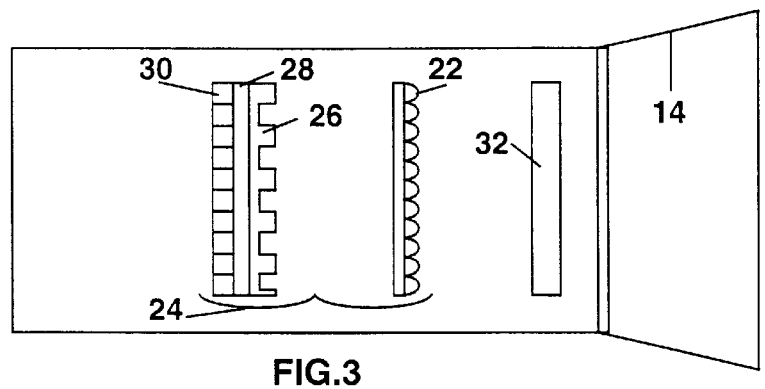
FIG. 3 is a diagrammatic illustration of one embodiment of the image enhancing system of FIG. 1 wherein a polarizing grid is mounted on the back surface of a retarder plate.
Figure 4:
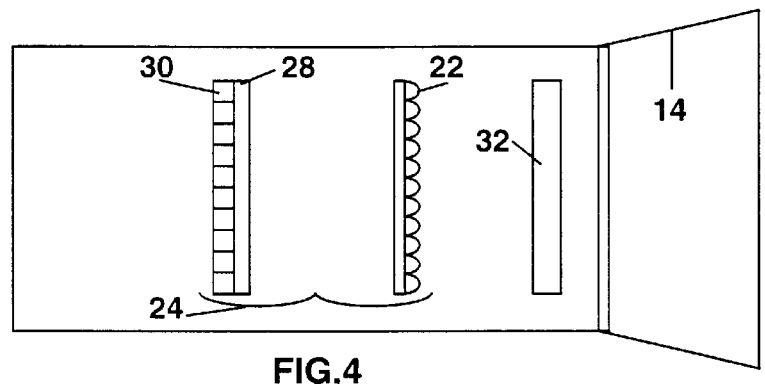
FIG. 4 is a view similar to FIG. 3 of another embodiment of the present invention in which the image enhancing assembly does not use a retarder plate and the polarizing grid is mounted on the focal plane array.
Figure 5:
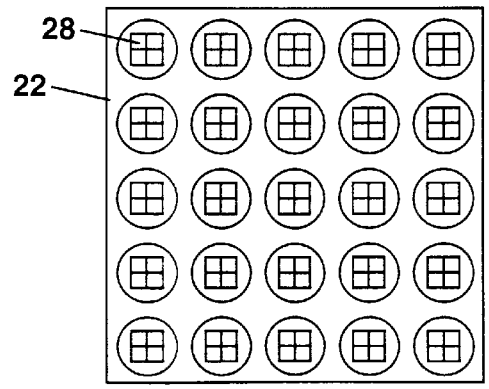
FIG. 5 is a front view of the lenslet array and illustrates the polarizing grid as being mounted on the front surface of each lens of the lenslet assembly of FIG. 1.

It is to be understood that the polarization matrix 28 (wire grid) may be mounted on the back surface 34 of retarder plate 26 and directly on sensor 30 as seen in FIG. 3 or in cases where a retarder plate is not used (FIG. 4) the polarization matrix 28 may be directly mounted on the sensor.

Referring again to FIG. 1, the electronic circuitry for processing the signals from sensor 30 is shown to include buffers 34. The buffers store the information received from one frame until additional information is received from a succeeding frame at which time the signals from the first frame is directed to a processor 36. The processor 36 processes the information received to sort out information relative to the Stokes vector. Processor 36 then directs this information to either a polarization processor 38 and/or a thermography processor 40. Processor 36 is connected to a control panel 42 which includes a multi-pole switch to control whether the output from processor 36 is directed to polarization processor 38 and/or thermography processor 40. If the polarization processor 38 is chosen to receive the signals from processor 36 then the polarization processor calculates the Stokes vector and directs signals indicative thereof to a polarization image data analyzer 39 which analyzes the Stokes vector and outputs information relative to the polarization data (DOLP, etc.) as discussed in the background of the invention.

Signals from the polarization image analyzers are then transmitted to the control panel 42 which then provides an output 44 which, in the imaging system disclosed, may be a video monitor 45. The monitor displays what the operator wants to look at, i.e., polarization data or thermal data. The control panel also controls what information is sent from processor 36.

If processor 36 is chosen to transmit thermal data of the image to the control panel 42 and video monitor 44, then signals from the processor 36 are sent to the thermography processor 40 for processing and the processed information is directed to a thermography image analyzer 46 and to control panel 42 and monitor 44.

Imaging device 10 is shown to also include a power module 46 connected to an AC adapter or battery indicated at 50. An AGC 52 provides gain control to control panel.

It is to be understood that while the output 44 is shown as being directed into a video monitor 45, the concept of the present invention also encompasses the ability of the output to be in data form or enhanced electrical signals which may be used to actuate other electrically actuatable devices.

FIGS. 6a–6g illustrate various patterns of the grids on the focal plane arrays.

For the patterns shown in FIG. 6a, a grid is placed on the focal plane array. Assume that the numbers 1, 2, 3, and 4 in FIG. 6a correspond to wire grids at 0, 45, 90 and 135 degrees respectively placed on the focal plane with (n×m) pixels. Appropriate grouping of the grids and suitable image processing on a pixel-by-pixel basis gives three of the four elements of the Strokes vector with spatial resolutions of a n−1×m−1. Each spot, designated by the letter "x" at the intersection of the grid corresponds to a polarization pixel, i.e., a "super" pixel at which the Stokes vector is calculated from the four pixels surrounding and joined at the intersection "x".

For the first spot, pixels 1, 2 on the first row and 3, 4 on the next row produce enough information to generate three of the four elements of the Stokes vector, for the next spot on the first row. The next pixels used are labeled 2, 3 on the first row and 4,1 on the second row. This is repeated for each intersection throughout the grid with an overall "polarization" resolution of 3×7.

Similarly for grids that are oriented every 22.5 degrees, eight pixels are used to produce a single polarization pixel as shown in FIG. 6b. In this case the polarization pixel ("super" pixel) is made up of focal plane array (FPA) pixels that takes on the shapes as shown in FIGS. 6c, 6d, 6e and 6f, or similar arrangements.

It should be noted that other combinations are possible, such as 9 FPA pixels to form one polarization pixel, i.e. "super pixel". In this case the orientation would be spaced every 20 degrees and use a 3×3 pixel grid.

Another arrangement (FIG. 6g) is shown to include a 12 pixel grid whose wire grids are placed every 15 degrees.

Figure 7:
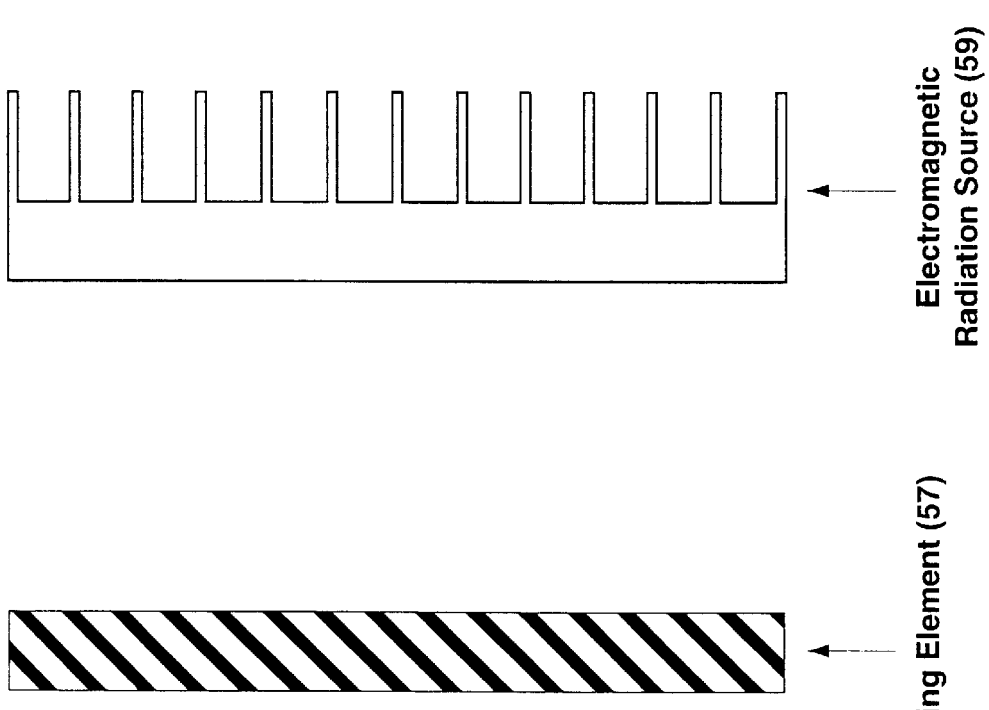
FIG. 7 is a diagrammatic view of a calibration device for FIG. 1.

The calibration device 32 is shown in FIG. 7 to include a polarizing element 57 and a radiation source 59. The radiation emitted by the source 59 is transmitted through the polarizing element 57 to produce a known polarization signal. This signal is then detected by the system. The output of the sensor can be used to calibrate the image enhancing system so that accurate measurements of the spatial phase vector of a scene may be performed.

Figure 8:
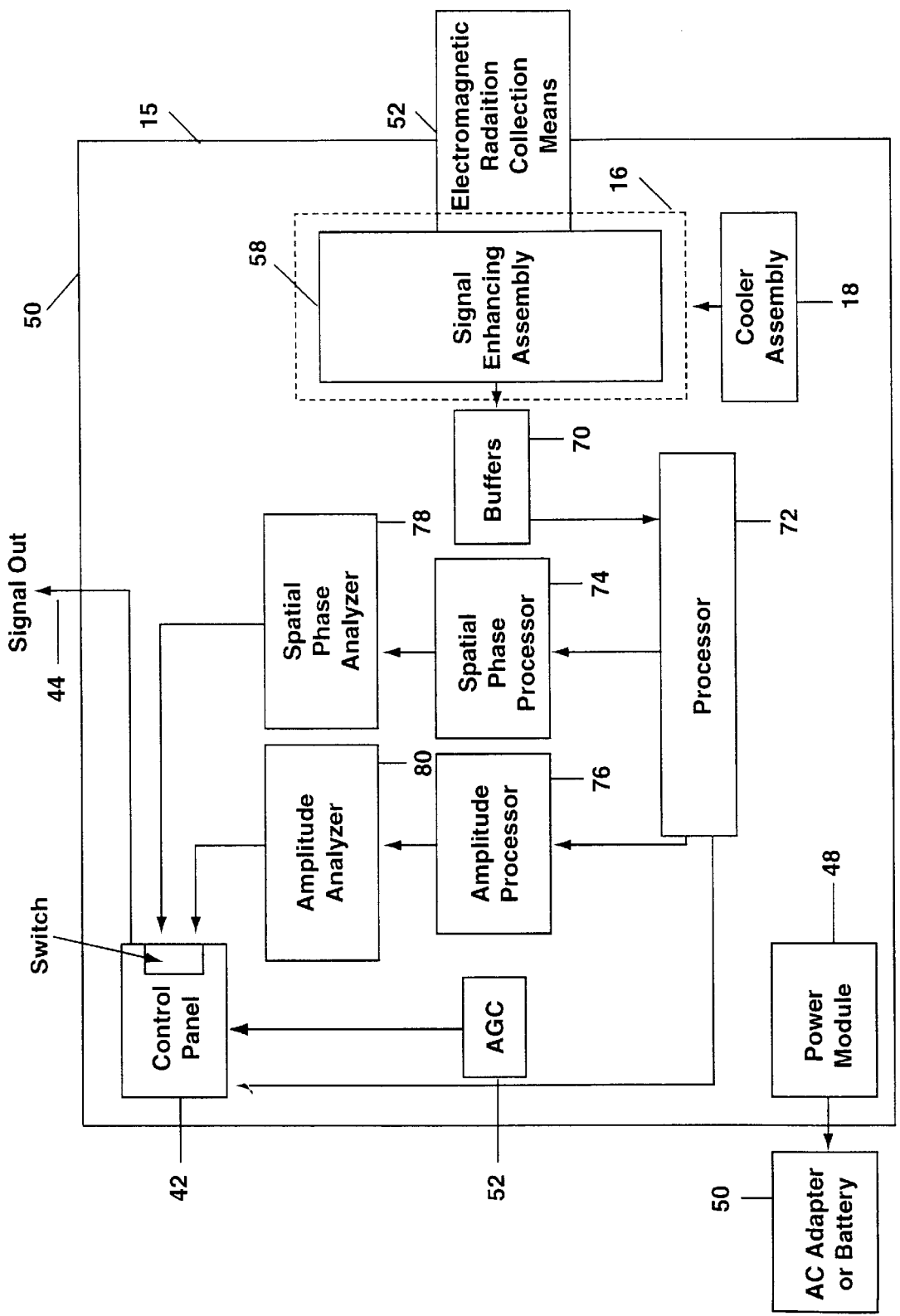
FIG. 8 is a view similar to FIG. 1 illustrating another embodiment of the present invention.

FIG. 8 illustrates another embodiment of the present invention wherein like numerals refer to like parts and wherein the spatial phase sensor is not limited to a video imaging system and provides for electromagnetic radiation signals across the electromagnetic spectrum to be enhanced.

As seen in FIG. 8, a housing 50 is shown to be provided with an electromagnetic radiation collection means 52, which may be a lens or aperture, through which electromagnetic radiation passes. Collection means 52 communicates into a Dewar assembly 16 which communicates with a cooler assembly 18 to provide coolant to components therein. Such Dewar assemblies are well known in the art. Carried in Dewar assembly 16 is an electromagnetic radiation signal enhancing assembly 58 which receives the radiation signals from collection means 52, and polarizes the electromagnetic radiation in a manner which will produce super pixels which greatly increases the signal-to-noise of the detected electromagnetic radiation.

The specific function of the signal enhancing assembly 58 is to form a plurality of pixels in predetermined patterns so that each pattern consists of at least four pixels formed in two rows and two columns with each pixel having different polarization vectors and the resultant output therefrom being taken from the point of adjoinment of the pixels in the form of a single output. An array of "super" pixels are formed in columns and rows by adjoining pluralities of the thus formed "super" pixels as discussed above.

Lenslet 22 (FIG. 3) described supra, is shown to be mounted behind radiation collection means 52 and is a part of a signal enhancing assembly 54 which includes a retarder plate 26, polarization matrix (wire grid) 28 and sensor 30. Polarization matrix 28 should be mounted close to the sensor 30. Sensor 30 receives the radiation and converts the radiation into electrical signals. Calibration device 32 may, if desired, be mounted intermediate the assembly 54 and radiation collection means 52 to calibrate the device, as discussed supra.

It is again pointed out that the polarization matrix 28 may be mounted on the back surface 34 of retarder plate 26 and directly on sensor 30 as seen in FIG. 3 or in cases where a retarder plate is not used (FIG. 4) the polarization matrix 28 may be directly mounted on the sensor 30.

Referring again to FIG. 8, the electronic circuitry for processing the signals from sensor 30 is shown to include buffers 70. The buffers store the information received from one frame until additional information is received from a succeeding frame at which time the signals from the first frame are directed to a processor 72. The processor 72 processes the information received to sort out information relative to the Stokes vector. Processor 72 then directs this information to either a spatial phase analyzer 74 and/or an amplitude processor 76. Processor 72 is connected to a control panel 42 which includes a multi-pole switch to control whether the output from processor 72 is directed to spatial phase processor 74 and/or amplitude processor 76. If the spatial phase processor 74 is chosen to receive the signals from processor 72 then the spatial phase processor calculates the Stokes vector and directs signals indicative thereof to a spatial phase analyzer 78 which analyzes the Stokes vector and outputs information relative to the polarization data (DOLP, etc.) as discussed in the background of the invention.

If the amplitude processor 76 is chosen to receive the signals from processor 72 then the amplitude of the received signals is processed to calculate raw intensity data from the measured spatial phase components and the processed amplitude signals are then transmitted to an amplitude analyzer 80 where the amplitude of the processed signals are analyzed to produce standard thermography images in the case of an infrared sensor.

Signals from the spatial phase analyzer 78 and the amplitude analyzer 80 are then transmitted to the control panel 42 which then provides an output 44.

Processor 72 may be any of many types of processors such as a 486 processor or the pentium processor pro having a 200 Mhz capacity. The processors 74 and 76 may be similar to the Texas Instrument DSP Model C-31 programmable processor. Polarization image analyzer 78 and thermography image analyzer 80 are standard analyzer digital filters, well known in the art.

The apparatus is shown to also include a power module 46 connected to an AC adapter or battery indicated at 50. An AGC 52 provides gain control to control panel.

It is to be understood that the output 44 may be in data form or enhanced electrical signals which may be used to actuate other electrically actuatable devices.

It is to be understood that the polarizer need not be contained in the housing and that it may be external and to the housing and in front of the lens. If the polarizer is external to the housing it is necessary that the polarizer be maintained at an intensity below that of the ambient intensity in which the system is to be used. The polarizer and radiation source do not necessarily have to be physically separate devices.

It is to be understood that although the polarizing element is described herein as a polarizing matrix in the form of a wire grid, it may also be any type of polarizing element, such as, a dichroic element, a diffraction grating, a thin film, etc.

It is to be also understood that the device of the present invention finds application in many areas. Some application areas are as follows: ATR sensor enhancement; surveillance and reconnaissance sensors; medical diagnosis imaging; spectroscopy; non-destructive testing; aging aircraft testing; ice detection; law enforcement (forensic, plate detection; etc.) fire fighting sensor; enhance weather sensor; MASINT collection sensor; hyperspectral sensor; failure analysis; kill assessment of missiles; space and stellar rejection (astronomy); target identification (range, poor weather); improved countermeasure resistant seeker; missile detection sensor (seeker, LBR); sniper in trees, mine detection and trip wires; FLIR enhancement; Night-sight enhancement; stress analysis sensor; communications (encryption and increased bandwidth); memory depth; and dual mode sensor for IR cameras. The above listing refers to only a few possible applications of the present invention, many other applications are possible.

The following is a discussion of some of the capabilities of the device of the present invention:

Multi-mode: Sensor can become truly multimode sensors. Polarization adds a new complementary set of data to the current Amplitude signal. Polarization is the 2-D spatial phase of the signal. Amplitude detection fused with spatial phase offers a dual mode common sensor system.

Extended Range Detection: Polarization signals are independent of signal amplitudes and is a phase detection system which eliminates noise (background). Polarization signals are strong even when there is no amplitude variations in signal. Polarization sensor naturally suppresses noise keeping the noise floor at the detector low allowing for extended range detection of polarized targets.

Enhanced Detection in Poor Weather: Works for all the same reasons as the extended Range Detection. It all deals with the scattering phenomena from the atmosphere. Polarization will suppress the scattered radiation while still detecting small percentages of polarized radiation.

High S/N at zero amplitude contrast: Emission from all surfaces is dependent on material type and orientation of surface. The phase components will vary as the angle of incidence changes. Amplitude data cannot be processed into phase elements, but phase elements can be processed to represent Amplitude. The breakdown of the phase will indicate high S/N even at low amplitudes and zero contrast. Variations in the signal, strong signals with no noticeable amplitude change, phase modulation with zero amplitude variation will all be measured to have strong and consistent spatial phase S/N.

Dynamic Real-time System: Polarization can be analyzed and recorded in real time. System can be extremely small and portable.

Maps Surface Orientations: As predicted by Fresnel's Laws, polarization changes with respect to the angle of incidence. The closer to grazing incidence the greater the polarization. This phenomena is similar to contrast shading which creates 3-D images. The polarization signature will be able to detect the object 3-D shape, and the object orientation. With the addition of circular polarization detection, material properties can be obtained by detecting the polarization ellipse of the light emitted by the surface. This is a form of ellipsometry.

Rejection of Scattered Radiation: The polarization filter will only allow a single orientation vector to pass through the filter, thus reducing the scattered radiation. This phenomena will provide enhanced detection capability for poor weather and other atmosphere attenuation, as well as detection through a dispersible medium. Scattered radiation from atmospheric attenuation will be reduced, thus increasing the detection range. Standard IR countermeasures such as jammers, and other hot unpolarized Lambertian sources, will be naturally rejected by the spatial phase sensor. Also on the complementary side, IR suppressors are similar to radiators which dissipate heat to maintain a lower temperature, many of these suppressors have thin vanes of metal to reduce heat, the thin vanes will be highly polarized.

While specific embodiments of the present invention are set forth herein, it is to be understood that various modifications may be resorted to that are within the spirit and scope of the appended claims. For example, the housing need not contain circuitry to detect and process thermal information if the operator only desires to examine polarized images. This would eliminate the requirement for thermal processing thereby eliminating the thermography processor 40, thermography image analyzer 46 and the switching mechanism of the control panel. The reverse is true if the operator only wishes to observe thermal images in which case the polarization processor 38 polarization image analyzer and switching mechanism of the control panel would be eliminated.

We claim:

1. A spatial phase sensor comprising:

means for collecting electromagnetic radiation signals;

signal enhancing means for receiving said electromagnetic radiation signals from said means for collecting said electromagnetic radiation signals and for providing an enhanced electrical signal therefrom, said signal enhancing means including:

means for producing an array of polarized super pixels, each pixel of said array of super pixels being defined by a plurality of pixels disposed in adjacent, adjoining relation and having discrete polarization vectors and a single super pixel as its output;

sensor means for converting said electromagnetic radiation signals into electrical signals containing data corresponding to the determined spatial phase of said electromagnetic radiation signals; and circuit means including means for analyzing said electromagnetic radiation signals to determine the spatial phase thereof by analysis of the polarization vectors of said electromagnetic radiation signals, said circuit means disposed for receiving said electrical signals from said sensor means and for processing said electrical signals to produce enhanced output signals containing said data corresponding to the determined spatial phase of said electromagnetic radiation.

2. A spatial phase sensor as in claim 1 wherein said signal enhancing means includes polarizing means for polarizing said electromagnetic radiation.

3. A spatial phase sensor as in claim 2 wherein said polarizing means includes a polarizing wire grid mounted in proximity of said sensor means, said wire grid disposed for producing pixels having discrete polarization vectors.

4. A spatial phase sensor as in claim 3 wherein said signal enhancing means includes a retarder plate having a front and rear surface, said retarder plate mounted between said lenslet array and said sensor means.

5. A spatial phase sensor as in claim 4 wherein said wire grid is mounted on or near said rear surface of said retarder plate.

6. A spatial phase sensor as in claim 5 including calibration means for calibrating said signal enhancing means.

7. A spatial phase sensor as in claim 2 wherein said sensor means is positioned behind said means for collecting electromagnetic radiation and said signal enhancing means further includes a lenslet array having a front and back surface, said lenslet array mounted intermediate said means for collecting said electromagnetic radiation and said sensor means, and, said polarizing means mounted on each lens of said lenslet array.

8. A spatial phase sensor as in claim 1 including calibration means for calibrating said signal enhancing means.

9. A spatial phase sensor as in claim 1 wherein said spatial phase sensor is a video imaging system.

10. A spatial phase sensor as in claim 9 wherein said video imaging system includes a housing for enclosing said signal enhancing means and said circuit means therein, said means for collecting said electromagnetic radiation being a lens mounted in said housing, said lens being disposed for directing an image of an object of interest into said housing and onto said sensor means.

11. A spatial phase sensor as set forth in claim 10 wherein said signal enhancing means is disposed for producing an array of polarized super pixels, each pixel of said array of super pixels being defined by a plurality of pixels disposed in adjacent, adjoining relation and having discrete polarization vectors and a single super pixel as its output.

12. A spatial phase sensor as in claim 11 wherein said signal enhancing means includes polarizing means for polarizing said image, and said sensor means being a focal plane array for converting said image into electrical signals for transmission to said circuit means.

13. A spatial phase sensor as in claim 12 wherein said polarizing means includes a polarizing wire grid mounted in proximity of said focal plane array, said wire grid disposed for producing pixels having discrete polarization vectors.

14. A spatial phase sensor as in claim 12 wherein said signal enhancing means includes said focal plane array mounted behind said lens, a lenslet array having a front and back surface, said lenslet array mounted intermediate said lens and said focal plane array, and said polarizing means being mounted on each lens of said lenslet array.

15. A spatial phase sensor as in claim 12 wherein said image enhancing means includes a retarder plate having a front and rear surface, said retarder plate mounted between said lenslet array and said focal plane array.

16. A spatial phase sensor as in claim 15 wherein said polarizing means for polarizing said image is a polarization wire grid mounted on said rear surface of said retarder plate.

17. A spatial phase sensor as in claim 9 wherein said circuit means includes first means in circuit for selectively receiving and processing only polarized data containing said spatial phase data from said signal enhancing means and second means in circuit for selectively receiving and processing only polarized thermal data from said signal enhancing means.

18. A spatial phase sensor as in claim 17 including a control panel for switching between said first and/or second means in circuit.

19. A spatial phase sensor comprising:

means for collecting electromagnetic radiation signals;

signal enhancing means for receiving said electromagnetic radiation signals from said means for collecting said electromagnetic signals and for providing an enhanced electrical signal therefrom, said signal enhancing means including means for producing a super pixel, said super pixel being defined by a plurality of pixels disposed in adjacent, adjoining relation and having discrete polarization vectors and a single super pixel as its output; and sensor means for converting said electromagnetic signals containing data corresponding to the determined spatial phase of said electromagnetic radiation signals and for providing an output containing said spatial phase data; and means for analyzing said electromagnetic radiation signals to determine the spatial phase thereof by analysis of the polarization vectors of said electromagnetic signals.

20. A spatial phase sensor as in claim 19 including means for producing an array of super pixels from said single super pixel by disposing a plurality of super pixels in rows and columns of adjacent adjoining super pixels.

* * * * *